(12) United States Patent
Bor

(10) Patent No.: US 7,708,408 B1
(45) Date of Patent: May 4, 2010

(54) SINGLE-ARM OPTICAL COHERENCE TOMOGRAPHY PACHYMETRY SYSTEM AND METHOD

(75) Inventor: Zsolt Bor, San Clemente, CA (US)

(73) Assignee: AMO Development LLC., Santa Ana, CA (US)

( * ) Notice: Subject to any disclaimer, the term of this patent is extended or adjusted under 35 U.S.C. 154(b) by 8 days.

(21) Appl. No.: 12/249,507

(22) Filed: Oct. 10, 2008

(51) Int. Cl.
*A61B 3/10* (2006.01)

(52) U.S. Cl. .................. 351/212; 351/205; 351/221

(58) Field of Classification Search .................. 351/205, 351/210, 212, 221, 246, 247
See application file for complete search history.

(56) References Cited

U.S. PATENT DOCUMENTS

| | | | |
|---|---|---|---|
| 5,491,524 A | 2/1996 | Hellmuth et al. | |
| 5,493,109 A | 2/1996 | Wei et al. | |
| 6,004,314 A | 12/1999 | Wei et al. | |
| 6,152,875 A * | 11/2000 | Hakamata | 600/319 |
| 2008/0151191 A1* | 6/2008 | McBeth | 351/212 |

* cited by examiner

*Primary Examiner*—Huy K Mai

(57) ABSTRACT

A single arm optical coherence tomography (OCT) pachymetry system and methods for measuring layers of the eye are disclosed. The system includes an artificial lens for positioning on the eye, a light source emitting a measurement light beam along an optical path posteriorly toward the cornea, and a detector receiving and measuring a combined signal of light reflections anteriorly from a plurality of reflecting surfaces associated with the eye. The reflecting surfaces include a first reflecting surface associated with the artificial lens and one or more second reflecting surfaces corresponding to corneal layers. A processor is coupled to the detector and is configured to determine a distance between two of the corneal layers from the combined signal.

20 Claims, 3 Drawing Sheets

SINGLE-ARM OPTICAL COHERENCE TOMOGRAPHY PACHYMETRY SYSTEM AND METHOD

BACKGROUND OF THE INVENTION

Field of the Invention

The present invention relates generally to measurements of tissues in the eye, and, more particularly, to methods and systems for measuring corneal layers of the eye using a single arm optical coherence tomography pachymeter.

Corneal shape corrective surgeries are commonly used to treat myopia, hyperopia, astigmatism, and the like. Procedures employing an excimer laser include laser assisted in-situ keratomileusis (LASIK), photo refractive keratectomy (PRK) and laser sub-epithelial keratomileusis (LASEK). During LASIK, a suction ring is typically placed over sclera tissue (the white part of the eye) to firmly hold the eye. A microkeratome with an oscillating steel blade can be used to make a partial incision through the front surface of a cornea and/or to automatically pass across the cornea to create a thin flap of tissue on the front central part of the eye. Alternatively, a femtosecond pulsed laser beam may be used to create a corneal flap. After the suction ring is removed, the flap is lifted to expose tissue for ablation with a laser. The laser is typically programmed to correct a desired amount of visual effect, and directs a laser beam at the exposed tissue. A rapid emission of laser pulses removes very small precise amounts of corneal tissue. After irrigation with saline solution, the corneal flap is folded back to heal in the pre-procedure or original position.

Many of these procedures require precise measurement of corneal thickness, layer depths and/or locations. One way of measuring is with optical coherence tomography (OCT). OCT measurements are generally based on Michelson interferometers, which separate light from a light source into two paths (sometimes referred to as arms) to a detector. A mirror (e.g., a reference mirror) is typically positioned in a first arm of the interferometer, and the eye is positioned in the second arm. In the first path, light from the light source reflects off a semi-transparent mirror (e.g., a beam splitter) to the reference mirror and then reflects back through the semi-transparent mirror to the detector. In the second path, light from the light source passes through the semi-transparent mirror, reflects off the eye to the semi-transparent mirror and then reflects from the semi-transparent mirror into the detector. The light from the two paths are analyzed and corneal thickness, layer depths or locations can be determined. Exemplary systems and methods for tomography of a cornea are described in U.S. Pat. Nos. 6,004,314, 5,491,524 and 5,493,109, the full disclosures of which are incorporated herein by reference.

In general, many ophthalmic procedures require measurements with an accuracy of about +/−5 µm or better. Many devices currently available for measuring corneal thickness are not capable of measuring to this accuracy. For example, many ultrasonic pachymeters (e.g., ultrasonic pachymeters manufactured by Sonogage, Inc., or Micro Medical Devices, Inc.) use 50 MHz acoustic transducers. The depth resolution of ultrasonic pachymeters at full width at half maximum (FWHM) is generally about 10-15 µm. The Artemis pachymeter manufactured by ArcScan, Inc., is a very high frequency three-dimension ultrasound pachymeter that claims a precision of 1 µm–5 µm but is very expensive and typically complex to operate. The Visante™ pachymeter manufactured by Carl Zeiss Meditec, Inc., is time domain OCT based and has a resolution of 17 µm (FWHM). The Fourier domain OCTs (such as developed by Bioptigen, Inc., Optoview Corp., etc.) usually use broader bandwidth light sources and more efficient FFT based algorithms. Fourier domain OCTs claim to have 6 µm resolution, but this number has not been confirmed by reliable, published measurement data. In addition, these Fourier domain OCTs currently lack a scanning diameter that approaches 9 mm.

An area of interest in many eye procedures is the location of Bowman's layer, usually used in creating a flap for surgery. A general problem with conventional OCTs is that the OCT signal level associated with Bowman's layer is very low (e.g., about the noise level). A further complication of time domain and Fourier domain OCTs is that minor movements of the eye (e.g., caused by head tremor or by the cardiac cycle) tend to deteriorate the depth resolution.

In light of the above, it would be desirable to have reliable, practical and affordable systems and devices to identify and measure the layers within the cornea. It would also be desirable that such systems and devices have an improved accuracy of about +/−5 µm.

BRIEF SUMMARY OF THE INVENTION

The present invention is generally directed to systems and methods using a single arm optical coherence tomography (OCT) pachymeter for measuring reflecting surfaces of an object disposed along an optical path and determining distances between the reflecting surfaces.

One embodiment discloses a method of measuring layers in an eye, where the layers of the eye include a plurality of corneal layer surfaces and the eye has an anterior orientation toward a cornea of the eye and a posterior orientation toward a retina of the eye. The method includes directing a light beam along an optical path posteriorly toward the cornea, generating a first signal by reflecting a first portion of the light beam anteriorly off a first corneal layer surface of the plurality of corneal layer surfaces, generating a second light signal by reflecting a second portion of the light beam anteriorly off a second corneal layer surface of the plurality of corneal layer surfaces, measuring a spectral content of a combined signal, and determining a separation distance between the first and second corneal layer surfaces based on the measured signal. The first signal and the second signal propagate as the combined signal anteriorly from the cornea.

In another embodiment, a method is disclosed for measuring a separation distance between layers of a cornea along an optical path, where the cornea has an artificial lens positioned thereon, and the artificial lens has a surface. The method includes directing a measurement light beam along the optical path posteriorly toward the cornea, reflecting anteriorly along the optical path from the cornea a combined light beam comprising a first light beam from the surface of the artificial lens and a second light beam from one or more surfaces corresponding to the layers of the cornea, and determining a separation distance between at least two of the layers of the cornea along the optical path by measuring the combined light beam. The surface of the artificial lens is configured to increase a contrast of detection associated with the one or more surfaces corresponding to the layers of the cornea.

In another embodiment, a single arm OCT pachymetry system for measuring layers in an eye is disclosed. The system includes an artificial lens configured to be positioned on the cornea, a light source emitting a measurement light beam along an optical path posteriorly toward the cornea, a detector configured to receive and measure a combined signal of reflections of light along the optical path anteriorly from a plurality of reflecting surfaces, and a processor coupled to the detector. The combined signal is based on the measurement light beam. The reflecting surfaces include a first reflecting surface associated with the artificial lens and one or more second reflecting surfaces corresponding to the plurality of corneal layer surfaces. The first reflecting surface is configured to increase a contrast of detection associated with the one or more second reflecting surfaces. The processor is configured to determine a distance between at least two of the plurality of corneal layer surfaces along the optical path based on the combined signal.

In some embodiments, a single arm OCT pachymetry system may be incorporated in, or combined with, other optical devices. In one embodiment, the pachymetry system is incorporated with a slitlamp microscope. In another embodiment, the pachymetry system is incorporated with a laser system operable to ablate the cornea.

BRIEF DESCRIPTION OF THE DRAWINGS

In the drawings, wherein like reference numerals refer to similar components.

DETAILED DESCRIPTION OF THE INVENTION

The present invention is particularly useful for enhancing accuracy and efficacy of laser eye surgical procedures, such as photorefractive keratectomy (PRK), phototherapeutic keratectomy (PTK), laser assisted in situ keratomileusis (LASIK), laser subepithelial keratomileusis (LASEK) and the like. Preferably, the present invention can provide enhanced optical accuracy of determining corneal thickness, layer depths and/or locations within the eye. While the system and methods of the present invention are described primarily in the context of a laser eye surgery system, it should be understood techniques of the present invention may be adapted for use in other procedures and systems where optical based interference is viable for sensing depth or structure within a material.

Systems and methods of the present invention permit rapid measurements of an object having reflecting and scattering surfaces, and are well-suited to rapidly measure a thickness and a tomography of a cornea, including various structures associated with the cornea (e.g., an air-tear film interface, an epithelium, Bowman's layer, an endothelium, and the like). Systems and methods of the present invention may also be integrated into other surgical equipment, such as a surgical laser, a slit lamp microscope, a suction ring, and the like.

Figure 1:
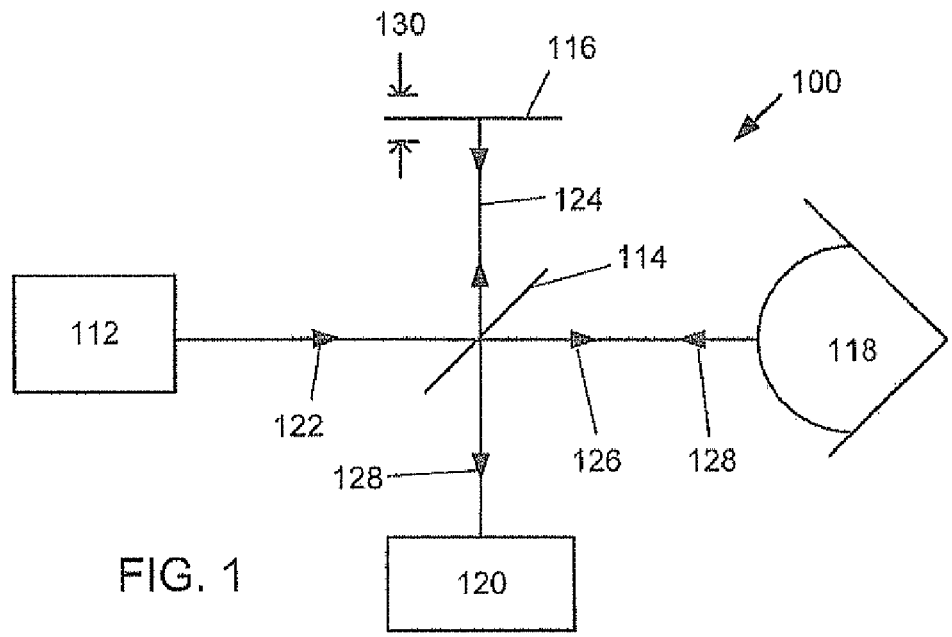
FIG. 1 is a block diagram of a Michelson interferometer using a two arm optical coherence tomography.

Measuring corneal thickness and tomography is typically done using optical coherence tomography (OCT) based on a Michelson interferometer. Referring to the drawings, a Michelson interferometer 110 is shown in FIG. 1 that includes a light source 112 producing a light beam 122, a semi-transparent mirror 114, a reference mirror 116, a cornea 118 and a detector 120. The semi-transparent mirror 114 operates as a beam-splitter and divides the light beam 122 into two paths 124 and 126, or arms, between the light source 112 and the detector 120. In one arm 124, a portion of the light beam 122 reflects from the semi-transparent mirror 114 to the reference mirror 116 and returns from the reference mirror 116 to pass through the semi-transparent mirror 114 to the detector 120. In another arm 126, a portion of the light beam 122 (e.g., different from the portion reflected by the mirror 114 in the other arm 124) passes through the semi-transparent mirror 114 to the cornea 118. Some of this light received by the cornea 118 reflects back to the semi-transparent mirror 114 and then reflects from the semi-transparent mirror 114 to the detector 120. At the semi-transparent mirror 114, the reflected light from the reference mirror 116 (e.g., along the path 124) and the reflected light from the cornea 118 (e.g., along the path 126) form a combined light beam 128. An interference pattern associated with this combined light beam 128 can be used for corneal tomography and measuring depths or thickness of various surface of the cornea 118.

A Michelson interferometer may use different methods of determining depths or layers from the reflected beams 124 and 126, such as a time domain OCT, a spectral OCT or a swept source OCT. In time domain OCT, the reference mirror 116 is movable 130 along a beam path, and this movement alters the combined light beam 128 interference pattern received by the detector 120. The corneal thickness and tomography can then be determined by analyzing the reference mirror 116 movement and the resulting interference pattern of the light beam 128 (e.g., based on the intensity thereof). In spectral OCT, the reference mirror 116 is fixed, and the detector 120 is a high speed spectrometer detector 120. A fast Fourier transform (FFT) is applied to the spectrometer signal (e.g., associated with the combined light beam 128) and used to calculate the layer structure of the cornea 118. In swept source OCT, the light source 112 is a tunable broadband light source 112. Swept source OCT is similar to spectral OCT except the detector 120 for swept source OCT is a photo detector and the wavelength of the light source is tunable. Analysis of the combined light beam 128 can be used to determine the layer structure of the cornea.

Figure 2:
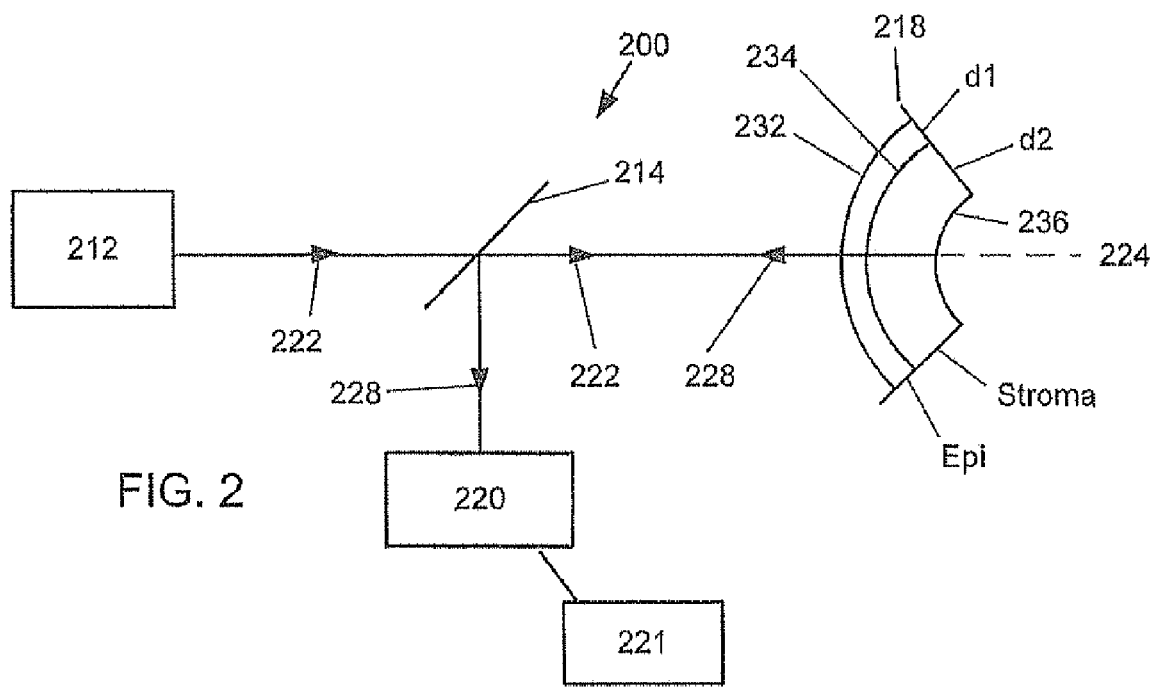
FIG. 2 is a block diagram of a single arm optical coherence tomography pachymeter in accordance with one embodiment.

FIG. 2 is a block diagram of a single arm OCT pachymeter 200 in one embodiment. The pachymeter 200 includes a light source 212, a semi-transparent mirror 214, and a detector 220. In contrast with conventional Michelson interferometers, the single arm OCT pachymeter 200 utilizes a single path or arm directed toward a cornea 218. Instead of the reference mirror used in two arm Michelson interferometers, the single arm OCT pachymeter 200 uses an at least partially reflecting surface along a single propagation path for a reference. In this embodiment, the light source 212 directs a measurement light beam 222 toward the semi-transparent mirror 214. The light source 212 may be an incandescent lamp, a broad spectrum light emitting diode (LED) (e.g., a white light LED), a laser, or other suitable light source.

The measurement light beam 222 incident on the semi-transparent mirror 214 passes through to the cornea 218 along a single arm beam (e.g., undivided by the mirror 214). Portions of the measurement light beam 222 reflect off different encountered surfaces associated with the cornea 218. Examples of different surfaces associated with the cornea 218 include, by way of example and not limitation, an anterior surface 232 (e.g., the air-tear film interface) of the epithelium, a posterior surface 234 of the epithelium or Bowman's layer, and a posterior surface 236 of the cornea 218 or endothelium. The measurement light beam 222 may also reflect off other reflecting layers or surfaces, such as the surface of an artificial lens (e.g., a contact lens or the like) positioned on the cornea 218. The reflected beams from the different layers or surfaces form a combined light beam 228 and return to the semi-transparent mirror 214, which reflects the combined light beam 228 from the semi-transparent mirror 214 to the detector 220. The detector 220 receives the combined light beam 228 for analysis.

A processor 221 may be coupled to the detector 220 to process the information the detector receives. For example, the processor 221 is configured to determine distances between two or more of the reflecting surfaces by analyzing the combined light beam 228. The processor 221 includes computer hardware and/or software (e.g., standard or proprietary digital and/or analog signal processing hardware, software, and/or firmware, a personal computer, a notebook computer, a tablet computer, a proprietary processing unit, or a combination thereof), and may utilize one or more programmable processor units running machine readable program instructions or code for implementing some or all of one or more of the methods described herein.

The code is embodied in a tangible media such as a memory (optionally a read only memory, a random access memory, a non-volatile memory, or the like) and/or a recording media (such as a floppy disk, a hard drive, a compact disc (CD), a digital video disc (DVD), a memory stick, or the like). The code and/or associated data and signals may also be transmitted to or from the processor 221 via a network connection (such as a wireless network, an Ethernet, the Internet, an intranet, or the like), and some or all of the code may also be transmitted between components of the single arm OCT pachymeter 200 and within the processor 221 via one or more bus, and appropriate standard or proprietary communications cards, connectors, cables, and the like may be included in the processor 221. The processor 221 is configured to perform the calculations and signal transmission steps described herein at least in part by programming the processor 221 with the software code, which may be written as a single program, a series of separate subroutines or related programs, or the like. Standard or proprietary input devices (such as a mouse, keyboard, touchscreen, joystick, etc.) and output devices (such as a printer, speakers, display, etc.) associated with computer systems may also be included, and processors having a plurality of processing units (or even separate computers) may be employed in a wide range of centralized or distributed data processing architectures.

To determine corneal thickness and tomography, the detector 220 and processor 221 analyze the combined light beam 228 received by the detector. Any suitable detector may be used. In one embodiment, the detector 220 is a high speed spectrometer that is configured to apply an FFT to the spectrometer signal associated with the combined light beam 228 to calculate the layer structure of the cornea. The interference of the beams alters the spectrum associated with light originating from the light source 212. This spectral change can be used to calculate and identify the layered structure of the eye (i.e., the depth location of the various layers and corresponding reflectivities). In another embodiment, the light source 212 is a swept light source in which the wavelength is tunable, and the detector 220 is photo detector.

Some of the advantages of the single arm OCT pachymeter 200 with respect to the Michelson type interferometer include but are not necessarily limited to:

1. Because the reference surface of the single arm OCT pachymeter 200 moves together with the eye, movement of the eye (e.g., associated with patient head movement, cardiac cycle, etc.) during measurement or treatment using this pachymeter generally does not affect the depth resolution;
2. High order group velocity dispersion is associated with the reference arm of the Michelson interferometer, but the single arm OCT pachymeter 200 is not complicated or limited by high order group velocity dispersion;
3. The group velocity dispersion associated with an achromat used in front of the cornea may influence the measurement of the Michelson-type OCTs but does not influence the measurement of the single arm OCT pachymeter 200;
4. Light beams in the single arm OCT pachymeter 200 can propagate in free space and thus, the use of single mode optical fibers can be avoided with this pachymeter 200;
5. Michelson-type OCTs typically use expensive superluminescence diode light sources. The single arm OCT pachymeter 200 can use inexpensive light sources such as incandescent lamps or white light LED. These inexpensive light sources are not only significantly less expensive, but also have much greater spectral width, which generally improves the depth resolution of the pachymeter 200; and
6. The single arm OCT pachymeter 200 has a depth resolution on the order of one (1) micron, in one embodiment.

The single arm OCT pachymeter 200 may also be combined with other devices for use in a variety of procedures. For example, the single arm OCT pachymeter 200 can be incorporated with a slitlamp at about half the cost associated with the conventional Michelson based OCT. When incorporated with the microscope of an excimer laser, real-time corneal thickness measurement can be performed prior to or during ablation. In a Placido type keratometer or a keratometer where the placido ring is replaced by a two-dimensional array of point light sources (e.g. an array of white light LED diodes), a three-dimensional image of the flap thickness or for diagnosing and predicting keratoconus can be obtained.

Figure 3A:
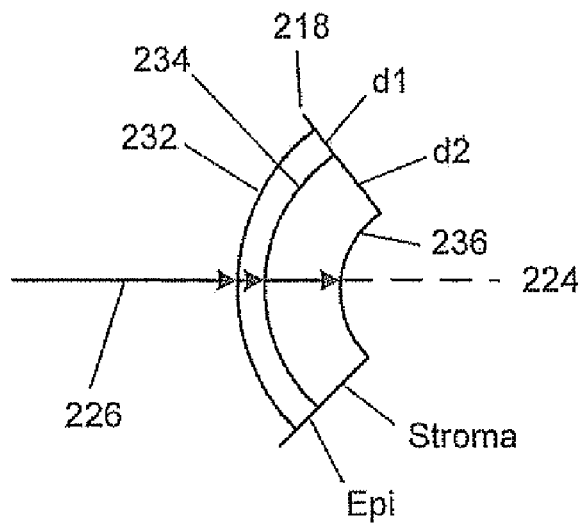
FIG. 3A is a sectional view of a cornea illustrating an optical path traversing posteriorly toward the cornea and intersecting corneal layers.

In one embodiment, the single arm OCT pachymeter 200 is configured to measure a separation distance between one or more corneal surfaces or layers. FIGS. 3A-3D are sectional views of a cornea 218 illustrating an optical path 224 associated with light traversing to and from various corneal surfaces or layers 232, 234, 236. Referring to FIGS. 2 and 3A-3D, for example, the single arm OCT pachymeter 200 can measure a first separation distance (d1) between an anterior surface 232 of the epithelium or an air-tear film interface, and an anterior surface 234 of the epithelium or Bowman's layer. Additionally, a second separation distance (d2) can be measured between the anterior surface 234 of the epithelium and a posterior surface 236 of the cornea or the endothelium. FIG. 3A shows a measurement light beam 226, such as the measurement light beam 222 from the light source 212 shown in FIG. 2, propagating along the optical path 224 posteriorly toward the cornea 218 and encountering the corneal surfaces 232, 234, 236.

Figure 3B:
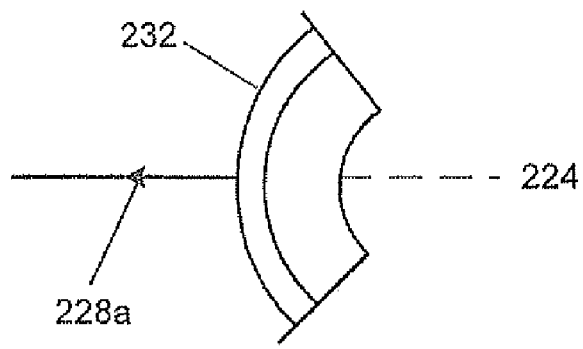
FIG. 3B is a sectional view of the cornea shown in FIG. 3A illustrating a light beam reflecting back anteriorly from a front surface of the epithelium or an air-tear film interface of the cornea.
Figure 3C:
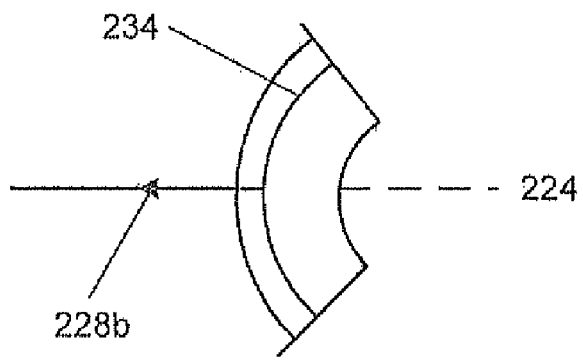
FIG. 3C is a sectional view of the cornea shown in FIG. 3A illustrating a light beam reflecting back anteriorly from the posterior surface of the epithelium or from Bowman's layer.
Figure 3D:
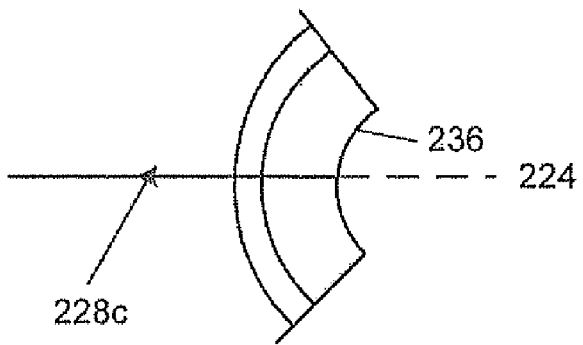
FIG. 3D is a sectional view of the cornea shown in FIG. 3A illustrating a light beam reflecting back anteriorly from the posterior of the cornea or from the endothelium.

As the measurement light beam 222 encounters each surface 232, 234, 236, some of the light associated with the measurement light beam 222 is reflected anteriorly back along the optical path 224. FIG. 3B shows a light beam 228a reflecting anteriorly back from the anterior surface 232 of the epithelium or the air-tear film interface. FIG. 3C shows a light beam 228b reflecting back anteriorly from the posterior surface 234 of the epithelium, or Bowman's layer. FIG. 3D shows a light beam 228c reflecting back anteriorly from the posterior 236 of the cornea, or endothelium.

Together, the reflected light beams 228a, 228b, 228c form a combined light beam 228 having an interference pattern. Separation distances may be determined between the reflecting corneal surfaces 232, 234, 236 along the optical path 224 by measuring this combined light beam 228 and using one of the reflecting corneal surfaces 232, 234, 236 as a reference surface. Any of the reflecting corneal surfaces 232, 234, 236 may be used, but the first reflecting surface may be preferred, such as the anterior surface 232 of the epithelium, the air-tear film interface, or a surface of an artificial lens (not shown) positioned on the cornea. The combined light beam 228 is received by the detector 220, such as a spectrometer discussed above. The optical path 224 may be repeated and moved to different locations around the cornea 218 to determine a tomography of the cornea 218, and this can be performed by directing the measurement beam 226 at the different locations (e.g., scanned).

Figure 4:
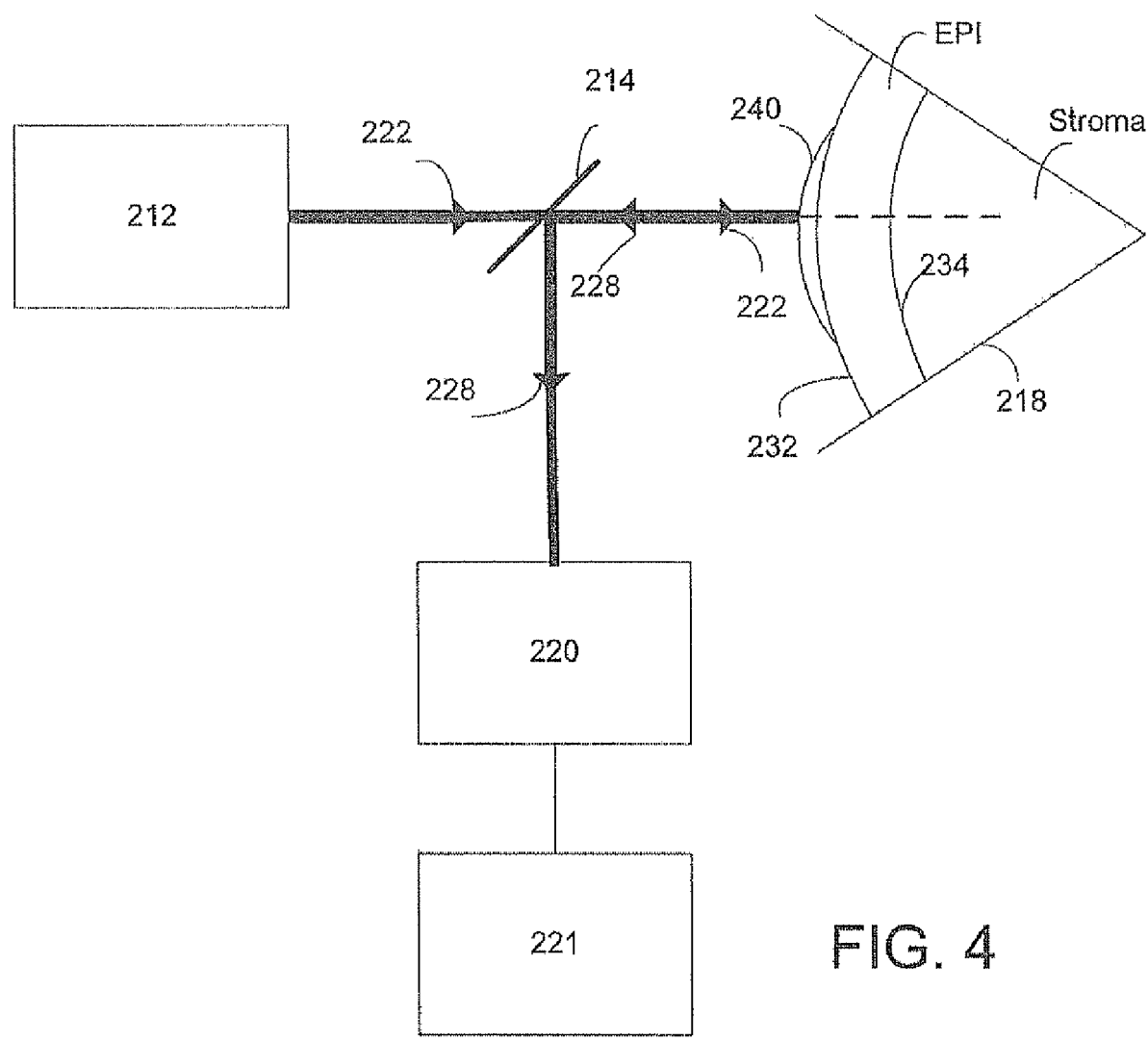
FIG. 4 is a block diagram of the single arm optical coherence tomography pachymeter shown in FIG. 2 in accordance with another embodiment.

Additionally, the single arm OCT pachymeter 200 can be used with a contact lens positioned onto the eye (e.g., onto the anterior surface of the cornea epithelium) to provide several advantages. FIG. 4 is a block diagram of the single arm optical coherence tomography pachymeter 200 shown in FIG. 2 in accordance with another embodiment. In this embodiment, a contact lens 240 is positioned onto the anterior surface 232 of the cornea 218. The surface of the contact lens 240 preferably has a reflectivity that is greater than the Fresnel reflectivity associated with the air-tear film interface. For example, the contact lens 240 can be formed with a very smooth anterior surface to increase the reflectivity of the anterior surface of the contact lens 240.

One advantage with using the contact lens 240 is to increase the contrast of detection (e.g., by the detector 220). The reflectivity of the anterior surface of the contact lens 240 can be increased significantly above the Fresnel reflectivity (e.g., about three-percent (3%) Fresnel reflectivity) typically associated with the air-tear film interface. For example, the reflectivity of the contact lens 240 can be increased to at least about ten-percent (10%) Fresnel reflectivity, and preferably between about ten-percent (10%) to about thirty-five percent (35%) Fresnel reflectivity. In a preferred embodiment, the reflectivity of the contact lens 240 is about thirty-percent (30%) Fresnel reflectivity. The contact lens can 240 also operate as a "spacer" to distance the high reflectivity surface associated with the contact lens 240 from the low reflectivity surface associated with Bowman's layer to improve signal detection and thus, improve discrimination of Bowman's layer as well as other corneal layers.

While the disclosure has been described in connection with specific embodiments thereof, it will be understood that it is capable of further modifications. This application is intended to cover any variations, uses, or adaptations of the disclosure following, in general, the disclosed principles and including such departures from the disclosure as come within known or customary practice within the art to which the disclosure pertains and as may be applied to the essential features hereinbefore set forth.

What is claimed is:

1. A method of measuring layers in an eye, the layers including a plurality of corneal layer surfaces, the eye defining an anterior orientation toward a cornea of the eye and a posterior orientation toward a retina of the eye, the method comprising the steps of:

directing a light beam along an optical path posteriorly toward the cornea;

generating a first signal by reflecting a first portion of the light beam anteriorly off a first corneal layer surface of the plurality of corneal layer surfaces;

generating a second light signal by reflecting a second portion of the light beam anteriorly off a second corneal layer surface of the plurality of corneal layer surfaces, wherein the first signal and the second signal propagate as a combined signal anteriorly from the cornea;

measuring a spectral content of the combined signal; and determining a separation distance between the first and second corneal layer surfaces based on the measured signal.

2. The method of claim 1, further comprising, prior to the step of directing, increasing a contrast of detection between the first corneal layer surface and the second corneal layer surface via a non-corneal surface.

3. The method of claim 2, wherein the step of increasing comprises positioning an artificial lens onto the cornea.

4. The method of claim 3, wherein the non-corneal surface comprises a surface of the artificial lens.

5. The method of claim 1, wherein the step of measuring comprises measuring a spectral content of the combined signal with a spectrometer.

6. The method of claim 1, wherein the step of measuring comprises determining a first intensity for the first portion of the light beam reflected from the first corneal layer surface and a second intensity for the second portion of the light beam reflected from the second corneal layer surface.

7. The method of claim 1, further comprising determining a tomography of the cornea by directing the measurement beam to several locations distributed across the cornea.

8. A method of measuring a separation distance between layers of a cornea along an optical path, the cornea having an artificial lens positioned thereon, the artificial lens having a surface, the method comprising:

directing a measurement light beam along the optical path posteriorly toward the cornea;

reflecting anteriorly along the optical path from the cornea a combined light beam comprising a first light beam from the surface of the artificial lens and a second light beam from one or more surfaces corresponding to the layers of the cornea, the surface of the artificial lens configured to increase a contrast of detection associated with the one or more surfaces corresponding to the layers of the cornea; and determining a separation distance between at least two of the layers of the cornea along the optical path by measuring the combined light beam.

9. The method of claim 8, wherein the step of reflecting comprises receiving the combined light beam with a detector.

10. The method of claim 9, wherein the detector comprises a spectrometer.

11. The method of claim 8, wherein the one or more second reflecting surfaces comprises a surface of the eye.

12. The method of claim 8, further comprising determining a tomography of the cornea by directing the measurement beam to several locations of the cornea.

13. A single arm optical coherence tomography (OCT) pachymetry system for measuring layers in an eye, the layers comprising a plurality of corneal layer surfaces, the eye defining an anterior orientation toward a cornea of the eye and a posterior orientation toward a retina of the eye, the system comprising:

an artificial lens configured to be positioned on the cornea;

a light source emitting a measurement light beam along an optical path posteriorly toward the cornea, a detector configured to receive and measure a combined signal of reflections of light along the optical path anteriorly from a plurality of reflecting surfaces, the combined signal based on the measurement light beam, the reflecting surfaces comprising a first reflecting surface associated with the artificial lens and one or more second reflecting surfaces corresponding to the plurality of corneal layer surfaces, the first reflecting surface configured to increase a contrast of detection associated with the one or more second reflecting surfaces; and a processor coupled to the detector, the processor configured to determine a distance between at least two of the plurality of corneal layer surfaces along the optical path based on the combined signal.

14. The system of claim 13, wherein the light source comprises one of the group consisting of an incandescent lamp, a white light LED, and a laser.

15. The system of claim 13, wherein the one or more second reflecting surfaces has a first Fresnel reflectivity, and wherein the first reflecting surface has a second Fresnel reflectivity that is about three times greater than the first Fresnel reflectivity.

16. The system of claim 13, wherein the first reflecting surface has a Fresnel reflectivity between about ten percent (10%) and about thirty-five percent (35%).

17. The system of claim 13, wherein the detector comprises a spectrometer.

18. The system of claim 13, further comprising a scanner optically coupled with the light source, the scanner comprising optical elements configured to direct the measurement light beam to locations across the cornea so as to measure a profile of the cornea with the measurement light beam.

19. The system of claim 13, wherein the system is configured to couple with a slit-lamp microscope.

20. The system of claim 13, wherein the system is configured to couple with a laser system, the laser system operable to ablate the cornea.

* * * * *